United States Patent
Riebel et al.

(10) Patent No.: US 6,645,915 B1
(45) Date of Patent: Nov. 11, 2003

(54) SUBSTITUTED 1,3,5- TRIAZINES

(75) Inventors: Hans-Jochem Riebel, Selters (DE); Akihiko Yanagi, Oyama (JP); Yukiyoshi Watanabe, Oyama (JP); Toshio Goto, Kokubunji-machi (JP); Kristian Kather, Köln (DE); Stefan Lehr, Langenfeld (DE); Katharina Voigt, Monheim (DE); Mark Wilhelm Drewes, Langenfeld (DE); Peter Dahmen, Neuss (DE); Dieter Feucht, Monheim (DE); Rolf Pontzen, Leichlingen (DE)

(73) Assignees: Nihon Bayer Agrochem K. K., Tokyo (JP); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/856,887

(22) PCT Filed: Nov. 25, 1999

(86) PCT No.: PCT/EP99/09102

§ 371 (c)(1), (2), (4) Date: Jul. 13, 2001

(87) PCT Pub. No.: WO00/32580

PCT Pub. Date: Jun. 8, 2000

(30) Foreign Application Priority Data

Dec. 1, 1998 (JP) .......................... 10-341671
May 27, 1999 (DE) .......................... 199 24 370

(51) Int. Cl.[7] ...................... C07D 251/18; A01N 43/68
(52) U.S. Cl. ...................... 504/234; 544/206; 544/207; 544/208; 544/209
(58) Field of Search ................. 544/206, 207, 544/208, 201, 209; 504/234

(56) References Cited

U.S. PATENT DOCUMENTS

| | | | |
|---|---|---|---|
| 2,961,377 A | 11/1960 | Sharpiro et al. | 167/65 |
| 3,816,419 A | 6/1974 | Cross et al. | 260/249.9 |
| 3,932,167 A | 1/1976 | Cross et al. | 71/93 |
| 5,290,754 A | 3/1994 | Nishii et al. | 504/232 |
| 5,403,815 A | 4/1995 | Nishii et al. | 504/230 |
| 5,750,788 A | 5/1998 | Häussling et al. | 564/415 |

FOREIGN PATENT DOCUMENTS

| | | |
|---|---|---|
| DE | 2141394 | 2/1972 |
| DE | 2258243 | 6/1973 |
| DE | 2532767 | 2/1976 |
| DE | 4131242 | 4/1993 |
| EP | 0 850 911 | 7/1998 |
| JP | 58-192873 | 11/1983 |
| JP | 52 025 796 | * 2/1997 |
| WO | 98/15537 | 4/1998 |

OTHER PUBLICATIONS

Shapiro et al. J. Amer.Chem.Soc. 81,3728–3736, 1959.*
Wakabayashi et al., Yuki Gosei Kagaku Kyokai Shi 28(3), 33–40, 1970, CA 72:132769, 1970.*
Fara et al., Pharmacol. Res. Commun. 6(2), 117–126,1974.*
Mayer et al. Agric. Biol. Chem, 45(2), 361–368, 1981.*
Chem. Abstracts 107:91770, Z. Naturforsh., C. Biosc (1987) 42, 663–669. The role of chirallty in the activity of photosystem II herbicides.
J. Org. Chem., vol. 33, Sep.–Dec. 1968, pp. 279–4280, Walter J. Gensler, Quazi A. Ahmed and Mervyn V. Leeding, Fluorination of Methyl Isobutyrate with Perchloryl Fluoride.

* cited by examiner

Primary Examiner—Richard L. Raymond
Assistant Examiner—Venkataraman Balasubramanian
(74) Attorney, Agent, or Firm—Richard E. L. Henderson; John E. Mrozinski, Jr.

(57) ABSTRACT

The invention relates to novel substituted 1,3,5-triazines of the general formula (I)

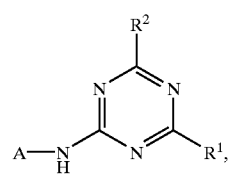

(I)

in which

A represents $CHR^3R^4$ or represents $C_1$-halogenoalkyl-substituted $C_3$–$C_6$-cycloalkyl, $C_3$–$C_6$-alkinyl or $C_1$–$C_4$-cyanoalkyl, where $R^1$, $R^2$, $R^3$ and $R^4$ are each as defined in the description, and to processes for their preparation, to novel intermediates, including their preparation, and to the use of the compounds of the general formula (I) as herbicides.

7 Claims, No Drawings

SUBSTITUTED 1,3,5- TRIAZINES

FIELD OF THE INVENTION

The invention relates to novel substituted 1,3,5-triazines, to processes and novel intermediates for their preparation and to their use as herbicides.

BACKGROUND OF THE INVENTION

Some substituted 1,3,5-triazines having herbicidal action have already been disclosed (see JP-A 19400/1961, U.S. Pat. Nos. 3,816,419, 3,932,167, JP-A 192873/1983, WO-A 90/09378). Likewise, the compounds (R)-6-chloro-N-(1-cyclohexyl-ethyl)-N'-ethyl-1,3,5-triazine-2,4-diamine, (S)-6-chloro-N-(1-cyclohexylethyl)-N'-ethyl-1,3,5-triazine-2,4-diamine and (R,S)-6-chloro-N-(1-cyclohexyl-ethyl)-N'-ethyl-1,3,5-triazine-2,4-diamine have already been disclosed in the literature as herbicidally active compounds (cf. Z. Naturforsch., C: Biosc. (1987), 42, 663–669—cited in Chem. Abstracts 107:91770). However, these compounds have hitherto not attained any particular importance.

SUMMARY OF THE INVENTION

Substituted cyclohexylalkylamino-1,3,5-triazines may be used as herbcides.

DETAILED DESCRIPTION

This invention, accordingly, provides novel substituted cyclohexylalkylamino-1,3,5-triazines of the general formula (I)

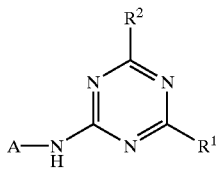

(I)

in which
- A represents $CHR^3R^4$ or represents $C_1$-halogenoalkyl-substituted $C_3$–$C_6$-cycloalkyl, $C_3$–$C_6$-alkinyl or $C_1$–$C_4$-cyanoalkyl, where
  - $R^3$ and $R^4$ simultaneously or independently of one another represent optionally cyano-, halogen- or $C_1$–$C_4$-alkoxy-substituted $C_1$–$C_6$-alkyl, represent $C_1$–$C_4$-halogenoalkyl or represent $C_3$–$C_7$-cycloalkyl which is optionally substituted by nitro, cyano, hydroxyl, halogen, by for its part in each case optionally cyano-, halogen- or $C_1$–$C_4$-alkoxy-substituted alkyl, alkoxy, alkylthio, alkylsulphinyl or alkylsulphonyl having in each case 1 to 6 carbon atoms or by for its part optionally cyano-, halogen- or $C_1$–$C_4$-alkyl-substituted cycloalkyl having 3 to 6 carbon atoms and where the total number of carbon atoms of $R^3$ and $R^4$ is greater than 3,
- $R^1$ represents amino, formylamino, represents dialkylaminoalkylideneamino having up to 6 carbon atoms, or represents in each case optionally cyano-, halogen- or $C_1$–$C_4$-alkoxy-substituted alkylcarbonylamino, alkoxycarbonyl-amino or alkylaminocarbonylamino having in each case 1 to 6 carbon atoms in the alkyl groups, and
- $R^2$ represents in each case optionally hydroxyl-, cyano-, halogen- or $C_1$–$C_4$-alkoxy-substituted alkyl, alkoxy, alkylcarbonyl, alkoxycarbonyl, alkylthio, alkylsulphinyl or alkylsulphonyl having in each case 1 to 6 carbon atoms or represents optionally cyano-, halogen- or $C_1$–$C_4$-alkyl-substituted cycloalkyl having 3 to 6 carbon atoms.

Preferred substituents or ranges of the radicals present in the formulae listed above and below are described below.

A preferably represents $CHR^3R^4$, preferably represents $C_1$-halogenoalkyl-substituted $C_5$–$C_6$-cycloalkyl, preferably represents 1,1-dimethyl-2-propinyl or preferably represents 1-cyano-1-methylethyl, where
- $R^3$ and $R^4$ preferably simultaneously or independently represent optionally cyano-, fluorine-, chlorine-, methoxy-, ethoxy-, n- or i-propoxy-substituted $C_1$–$C_5$-alkyl, represent $C_1$–$C_3$-halogenoalkyl or represent $C_3$–$C_6$-cycloalkyl which is optionally substituted by nitro, cyano, hydroxyl, fluorine, chlorine, bromine, by for its part in each case optionally cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, or by for its part in each case optionally cyano-, fluorine-, chlorine-, bromine-, methyl-, ethyl-, n- or i-propyl-, n-, i-, s- or t-butyl-substituted cyclopropyl, cyclobutyl, cyclopentyl or cyclohexyl, and where the total number of carbon atoms of $R^3$ and $R^4$ is greater than 3, $R^1$ preferably represents amino, formylamino, dimethylaminomethyleneamino or diethylaminomethyleneamino, or represents in each case optionally cyano-, fluorine-, chlorine-, methoxy-, ethoxy-, n- or i-propoxy-substituted acetyl-amino, propionylamino, n- or i-butyroylamino, methoxycarbonylamino, ethoxycarbonylamino, n- or i-propoxycarbonylamino, methylaminocarbonylamino, ethylaminocarbonylamino, n- or i-propylaminocarbonylamino.

$R^2$ preferably represents in each case optionally hydroxyl-, cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, acetyl, propionyl, n- or i-butyroyl, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, or represents in each case optionally cyano-, fluorine-, chlorine-, methyl- or ethyl-substituted cyclopropyl, cyclobutyl, cyclopentyl or cyclohexyl.

A particularly preferably represents $CHR^3R^4$, represents trifluoromethyl-substituted cyclohexyl, represents 1,1-dimethyl-2-propinyl or represents 1-cyano-1-methylethyl, where
- $R^3$ and $R^4$ particularly preferably simultaneously or independently represent in each case optionally cyano-, fluorine-, chlorine-, methoxy-, ethoxy-, n- or i-propoxy-substituted methyl, ethyl, n- or i-propyl, n-, s-, i- or t-butyl, represent 2-fluoroethyl, 2-chloroethyl, 1-fluoroethyl, 3-fluoropropyl or 3-chloropropyl or represent cyclopentyl or cyclohexyl, where the cycloalkyl radicals are optionally substituted by hydroxyl, fluorine, chlorine, by for its part in each case optionally fluorine-, chlorine-, methoxy-, ethoxy-, n- or i-propoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, or by for its part in each case optionally fluorine-, chlorine-, methyl-, ethyl-, n- or i-propyl-substituted cyclohexyl, and where the total number of carbon atoms of $R^3$ and $R^4$ is greater than 3, $R^1$ particularly preferably represents amino, formylamino, dimethylaminomethyleneamino, acetylamino or propionylamino.

$R^2$ particularly preferably represents in each case optionally fluorine-, chlorine-, methoxy-, ethoxy-substituted methyl, ethyl, n- or i-propyl.

A very particularly preferably represents $CHR^3R^4$, represents trifluoromethyl-substituted cyclohexyl, represents 1,1-dimethyl-2-propinyl or represents 1-cyano-1-methylethyl, where
$R^3$ and $R^4$ very particularly preferably simultaneously or independently represent methyl, ethyl, n- or i-propyl, represent 2-fluoroethyl, 2-chloroethyl, 1-fluoroethyl, 3-fluoropropyl or 3-chloropropyl or represent cyclopentyl or cyclohexyl and where the total number of carbon atoms of $R^3$ and $R^4$ is greater than 3.

$R^1$ very particularly preferably represents amino, formylamino, ethylcarbonylamino or methylcarbonylamino.

$R^2$ very particularly preferably represents 1-fluoroethyl, difluorochloromethyl, dichloromethyl or 1-fluoro-1-methylethyl.

The abovementioned general or preferred radical definitions apply both to the end products of the formula (I) and, correspondingly, to the starting materials or intermediates required in each case for the preparation. These radical definitions can be combined with each other as desired, i.e. including combinations between the given preferred ranges.

Preference according to the invention is given to those compounds of the formula (I) which contain a combination of the meanings listed above as being preferred.

Particular preference according to the invention is given to those compounds of the formula (I) which contain a combination of the meanings mentioned above as being particularly preferred.

Very particular preference according to the invention is given to those compounds of the formula (I) which contain a combination of the meanings listed above as being very particularly preferred.

Halogen represents fluorine, chlorine, bromine or iodine, preferably fluorine, chlorine or bromine.

Saturated or unsaturated hydrocarbon radicals, such as alkyl,—also in combination with heteroatoms, such as in alkoxy—are in each case straight-chain or branched as far as this is possible. $C_1$–$C_6$-alkyl represents, for example, methyl, ethyl, n- and i-propyl, n-, s-, i- or t-butyl, n-, i-, t- or neo-pentyl, n-, i-, s-, t- or neo-hexyl inter alia.

Likewise, alkinyl radicals can in each case be straight-chain or branched. $C_2$–$C_6$-alkinyl represents, for example, ethinyl, 1-propinyl, 2-propinyl, 1-methyl-2-propinyl, 1,1-dimethyl-2-propinyl, 1-ethyl-2-propinyl inter alia.

The following radicals may be mentioned by way of example for optionally substituted cycloalkyl radicals: cyclopropyl, 2-methylcyclopropyl, 2-chlorocyclopropyl, cyclobutyl, cyclopentyl, 3-methylcyclopentyl, 2-fluorocyclopentyl, cyclohexyl, 4-methylcyclohexyl, 2-fluorocyclohexyl, cycloheptyl etc.

Halogenoalkyl radicals which may be mentioned by way of example are: fluoromethyl, trifluoromethyl, 2-fluoroethyl, 2-chloroethyl, 2-bromoethyl, 2,2,2-trifluoroethyl, 1-fluoroethyl, 3-fluoropropyl, 3-chloropropyl etc.

Cyano-substituted alkyl radicals which may be mentioned by way of example are: cyanomethyl, 1-cyanoethyl, 2-cyanoethyl, 3-cyanopropyl, 1-cyanopropyl, 1-cyano-1-methylethyl, 4-cyanobutyl etc.

Alkylcarbonyl radicals which may be mentioned by way of example are: methylcarbonyl, ethylcarbonyl, n-propylcarbonyl, i-propylcarbonyl, n-butylcarbonyl etc.

Optionally substituted radicals can be mono- or polysubstituted, and in the case of polysubstitution, the substituents can be identical or different.

The compounds of the general formula (I) according to the invention contain at least one asymmetrically substituted carbon atom, and they can therefore be present in different enantiomeric (R- and S-configured forms) or diasteromeric forms. The invention relates both to the different possible individual enantiomeric or stereoisomeric forms of the compounds of the general formula (I) and to the mixtures of these isomeric compounds.

The novel substituted 1,3,5-triazines of the general formula (I) have interesting biological properties. In particular, they have strong herbicidal action.

Examples of compounds of the general formula (I) are listed in Table 1 below.

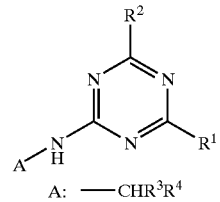

A: —$CHR^3R^4$

| $R^1$ | $R^2$ | $R^3$ | $R^4$ |
|---|---|---|---|
| $NH_2$ | $(CH_3)_2CF$ | $CH_3$ | $n\text{-}C_3H_7$ |
| NHCHO | $(CH_3)_2CF$ | $CH_3$ | $n\text{-}C_3H_7$ |
| $NHCOCH_3$ | $(CH_3)_2CF$ | $CH_3$ | $n\text{-}C_3H_7$ |
| $NHCOC_2H_5$ | $(CH_3)_2CF$ | $CH_3$ | $n\text{-}C_3H_7$ |
| $NHCOC_2H_5$ | $CH_3CHF$ | $CH_3$ | $i\text{-}C_3H_7$ |
| $NH_2$ | $CH_3CHF$ | $CH_3$ | $i\text{-}C_4H_9$ |
| NHCHO | $CH_3CHF$ | $CH_3$ | $i\text{-}C_4H_9$ |
| $NHCOCH_3$ | $CH_3CHF$ | $CH_3$ | $i\text{-}C_4H_9$ |
| $NHCOC_2H_5$ | $CH_3CHF$ | $CH_3$ | $i\text{-}C_4H_9$ |
| $NH_2$ | $(CH_3)_2CF$ | $CH_3$ | $i\text{-}C_4H_9$ |
| NHCHO | $(CH_3)_2CF$ | $CH_3$ | $i\text{-}C_4H_9$ |
| $NHCOCH_3$ | $(CH_3)_2CF$ | $CH_3$ | $i\text{-}C_4H_9$ |
| $NHCOC_2H_5$ | $(CH_3)_2CF$ | $CH_3$ | $i\text{-}C_4H_9$ |
| $NH_2$ | $(CH_3)_2CF$ | $CH_3$ | $(CH_3)_2CHCH_2CH_2CH_2$ |
| NHCHO | $(CH_3)_2CF$ | $CH_3$ | $(CH_3)_2CHCH_2CH_2CH_2$ |
| $NHCOC_2H_5$ | $(CH_3)_2CF$ | $CH_3$ | $(CH_3)_2CHCH_2CH_2CH_2$ |
| $NH_2$ | $CH_3CHF$ | $C_2H_5$ | $C_2H_5$ |
| NHCHO | $CH_3CHF$ | $C_2H_5$ | $C_2H_5$ |
| $NHCOCH_3$ | $CH_3CHF$ | $C_2H_5$ | $C_2H_5$ |
| $NHCOC_2H_5$ | $CH_3CHF$ | $C_2H_5$ | $C_2H_5$ |
| $NH_2$ | $(CH_3)_2CF$ | $C_2H_5$ | $C_2H_5$ |
| NHCHO | $(CH_3)_2CF$ | $C_2H_5$ | $C_2H_5$ |
| $NHCOCH_3$ | $(CH_3)_2CF$ | $C_2H_5$ | $C_2H_5$ |
| $NHCOC_2H_5$ | $(CH_3)_2CF$ | $C_2H_5$ | $C_2H_5$ |
| $NH_2$ | $CH_3CHF$ | $C_2H_5$ | $n\text{-}C_3H_7$ |
| NHCHO | $CH_3CHF$ | $C_2H_5$ | $n\text{-}C_3H_7$ |
| $NHCOCH_3$ | $CH_3CHF$ | $C_2H_5$ | $n\text{-}C_3H_7$ |

-continued

| | | | |
|---|---|---|---|
| NHCOC₂H₅ | CH₃CHF | C₂H₅ | n-C₃H₇ |
| NH₂ | (CH₃)₂CF | C₂H₅ | n-C₃H₇ |
| NHCHO | (CH₃)₂CF | C₂H₅ | n-C₃H₇ |
| NHCOCH₃ | (CH₃)₂CF | C₂H₅ | n-C₃H₇ |
| NHCOC₂H₅ | (CH₃)₂CF | C₂H₅ | n-C₃H₇ |
| NH₂ | (CH₃)₂CF | C₂H₅ | i-C₃H₇ |
| NHCHO | (CH₃)₂CF | C₂H₅ | i-C₃H₇ |
| NH₂ | (CH₃)₂CF | C₂H₅ | n-C₄H₉ |
| NHCHO | (CH₃)₂CF | C₂H₅ | n-C₄H₉ |
| NH₂ | (CH₃)₂CF | C₂H₅ | sec-C₄H₉ |
| NHCHO | (CH₃)₂CF | C₂H₅ | sec-C₄H₉ |
| NH₂ | (CH₃)₂CF | C₂H₅ | i-C₄H₉ |
| NHCHO | (CH₃)₂CF | C₂H₅ | i-C₄H₉ |
| NH₂ | (CH₃)₂CF | C₂H₅ | tert-C₄H₉ |
| NHCHO | (CH₃)₂CF | C₂H₅ | tert-C₄H₉ |
| NH₂ | (CH₃)₂CF | C₂H₅ | cyclo-C₃H₅ |
| NHCHO | (CH₃)₂CF | C₂H₅ | cyclo-C₃H₅ |
| NH₂ | (CH₃)₂CF | C₂H₅ | cyclo-C₅H₉ |
| NHCHO | (CH₃)₂CF | C₂H₅ | cyclo-C₅H₉ |
| NH₂ | (CH₃)₂CF | C₂H₅ | cyclo-C₆H₁₁ |
| NHCHO | (CH₃)₂CF | C₂H₅ | cyclo-C₆H₁₁ |
| NH₂ | (CH₃)₂CF | C₂H₅ | FCH₂CH₂ |
| NH₂ | (CH₃)₂CF | C₂H₅ | ClCH₂CH₂ |
| NH₂ | (CH₃)₂CF | C₂H₅ | CH₃CHF |
| NH₂ | (CH₃)₂CF | C₂H₅ | FCH₂CH₂CH₂ |
| NH₂ | (CH₃)₂CF | C₂H₅ | ClCH₂CH₂CH₂ |
| NH₂ | (CH₃)₂CF | n-C₃H₇ | n-C₃H₇ |
| NH₂ | (CH₃)₂CF | n-C₃H₇ | i-C₃H₇ |
| NH₂ | (CH₃)₂CF | n-C₃H₇ | n-C₄H₉ |
| NH₂ | (CH₃)₂CF | i-C₃H₇ | i-C₃H₇ |
| NH₂ | (CH₃)₂CF | i-C₃H₇ | n-C₄H₉ |
| NH₂ | (CH₃)₂CF | n-C₄H₉ | n-C₄H₉ |
| NH₂ | (CH₃)₂CF | n-C₄H₉ | i-C₄H₉ |
| NH₂ | (CH₃)₂CF | n-C₅H₁₁ | n-C₅H₁₁ |

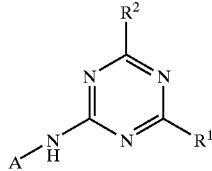

| A | R¹ | R² |
|---|---|---|
| 2-CF₃-cyclo-C₆H₁₀ | NH₂ | (CH₃)₂CF |
| 3-CF₃-cyclo-C₆H₁₀ | NH₂ | CH₃CHF |
| 3-CF₃-cyclo-C₆H₁₀ | NHCHO | CH₃CHF |
| 3-CF₃-cyclo-C₆H₁₀ | NHCOCH₃ | CH₃CHF |
| 3-CF₃-cyclo-C₆H₁₀ | NHCOC₂H₅ | CH₃CHF |
| 3-CF₃-cyclo-C₆H₁₀ | NH₂ | (CH₃)₂CF |
| 3-CF₃-cyclo-C₆H₁₀ | NHCHO | (CH₃)₂CF |
| 3-CF₃-cyclo-C₆H₁₀ | NHCOCH₃ | (CH₃)₂CF |
| 3-CF₃-cyclo-C₆H₁₀ | NHCOC₂H₅ | (CH₃)₂CF |
| 4-CF₃-cyclo-C₆H₁₀ | NH₂ | CH₃CHF |
| 4-CF₃-cyclo-C₆H₁₀ | NHCHO | CH₃CHF |
| 4-CF₃-cyclo-C₆H₁₀ | NHCOCH₃ | CH₃CHF |
| 4-CF₃-cyclo-C₆H₁₀ | NHCOC₂H₅ | CH₃CHF |
| 4-CF₃-cyclo-C₆H₁₀ | NH₂ | (CH₃)₂CF |
| 4-CF₃-cyclo-C₆H₁₀ | NHCHO | (CH₃)₂CF |
| 4-CF₃-cyclo-C₆H₁₀ | NHCOCH₃ | (CH₃)₂CF |
| 4-CF₃-cyclo-C₆H₁₀ | NHCOC₂H₅ | (CH₃)₂CF |
| 1,1-dimethyl-2-propyl | NH₂ | (CH₃)₂CF |
| 1-cyano-1-methylethyl | NH₂ | (CH₃)₂CF |

The novel substituted 1,3,5-triazines of the general formula (I) are obtained when (a) biguanides of the general formula (II)

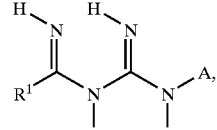

in which

A and $R^1$ are each as defined above, and/or acid adducts of compounds of the general formula (II)

are reacted with alkoxycarbonyl compounds of the general formula (III)

$$R^2\text{—CO—}OR^5 \tag{III},$$

in which $R^2$ is as defined above and $R^5$ represents alkyl, if appropriate in the presence of a reaction auxiliary and if appropriate in the presence of a diluent and if appropriate the resulting compounds of the general formula (I) are subjected to further conversions within the scope of the definition of the substituents, by customary methods, or (b) 1,3,5-triazines of the formula (Ia) in which $R^1$ represents amino

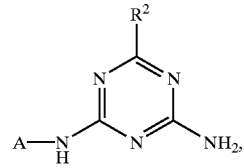

where A and $R^2$ are as defined above, are reacted with carbonyl halides of the general formula (IV)

$$R^6X^2 \tag{IV}$$

where $R^6$ represents formyl or represents optionally cyano-, halogen- or $C_1$–$C_4$-alkoxy-substituted alkylcarbonyl having in each case 1 to 6 carbon atoms in the alkyl group and $X^2$ represents chlorine or bromine, in the presence of a diluent and, if appropriate, in the presence of a base, or (c) the compounds of the general formula (Ia) in which $R^1$ represents amino are reacted with carboxylic anhydrides of the general formula (V)

$$R^6OR^6 \tag{V},$$

where $R^6$ is as defined above, in the presence of a diluent and, if appropriate, in the presence of a base, or (d) the compounds of the general formula (Ia) in which $R^1$ represents amino are reacted with carboxylic esters of the general formula (VI)

R⁶OR⁵ (VI), where
R⁵ and R⁶ are each as defined above,
in the presence of a diluent and, if appropriate, in the presence of a base, or (e) the compounds of the general formula (Ia) in which R¹ represents amino are reacted with carboxylic acids of the general formula (VII)

R⁶OH (VII), where
R⁶ is as defined above,
in the presence of a diluent and, if appropriate, in the presence of a condensing agent.

Using, for example, 1-(1-cyclohexyl-ethyl)-biguanide and methyl trifluoroacetate as starting materials, the course of the reaction in the process (a) according to the invention can be illustrated by the following formula scheme:

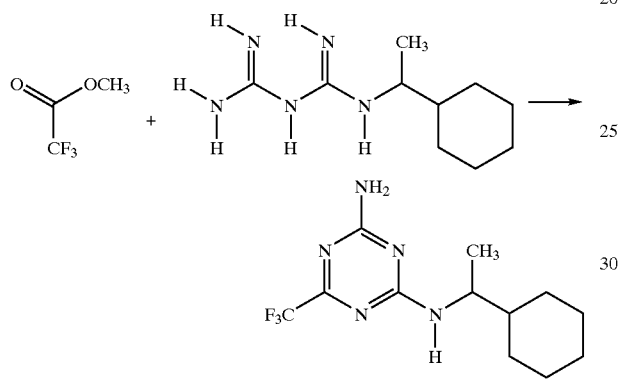

Using, for example, the hydrogen chloride adduct of 1-(1-ethylpropyl)-biguanide and methyl 1-fluoro-1-methylacetate as starting material, the course of the reaction in the process (a) according to the invention can be illustrated by the following formula scheme:

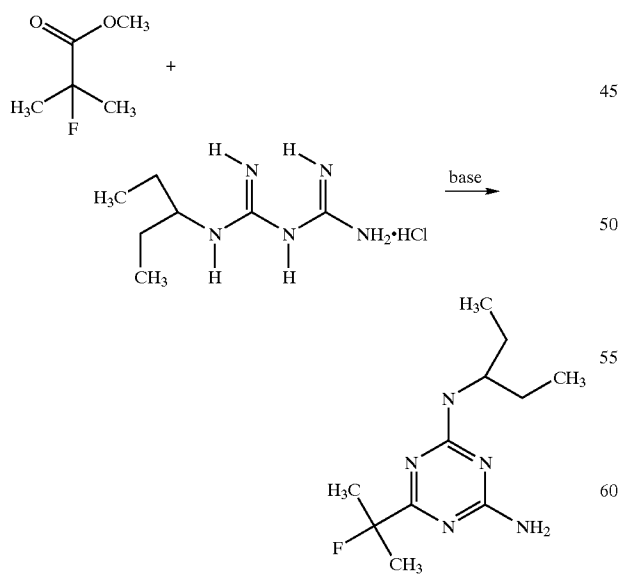

Using, for example, N-(1-ethylpropyl)-6-(1-fluoro-1-methylethyl)-1,3,5-triazine-2,4-diamine and acetyl chloride as starting materials, the course of the reaction in the process (b) according to the invention can be illustrated by the following formula scheme:

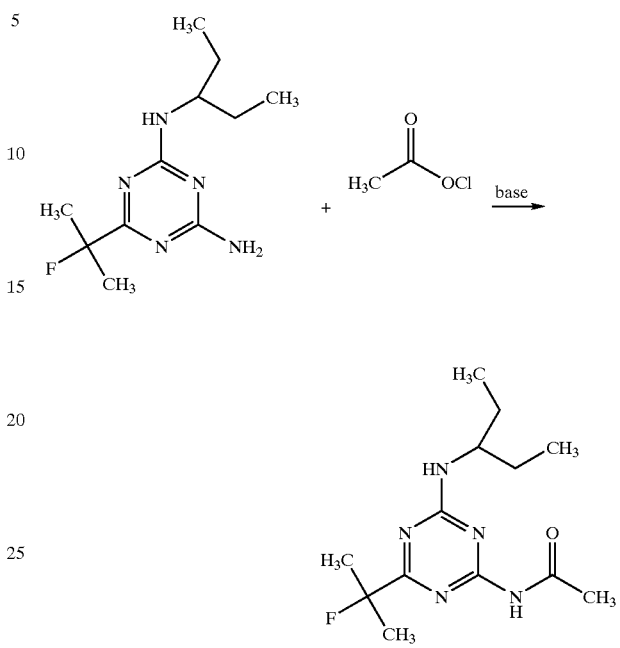

Using, for example, N-(1-ethylpropyl)-6-(1-fluoro-1-methylethyl)-1,3,5-triazine-2,4-diamine and acetic anhydride as starting materials, the course of the reaction in the process (c) according to the invention can be illustrated by the following formula scheme:

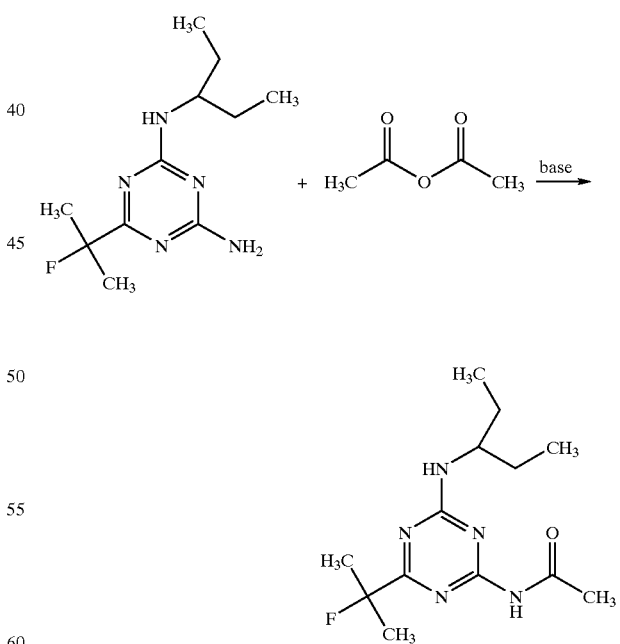

Using, for example, N-(1-ethylpropyl)-6-(1-fluoro-1-methylethyl)-1,3,5-triazine-2,4-diamine and ethyl acetate as starting materials, the course of the reaction in the process (d) according to the invention can be illustrated by the following formula scheme:

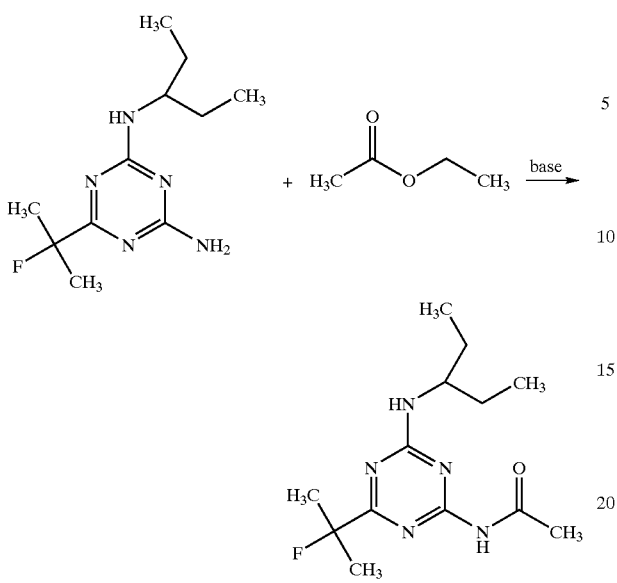

Using, for example, N-(1-ethylpropyl)-6-(1-fluoro-1-methylethyl)-1,3,5-triazine-2,4-diamine and acetic acid as starting materials, the course of the reaction in the process (e) according to the invention can be illustrated by the following formula scheme:

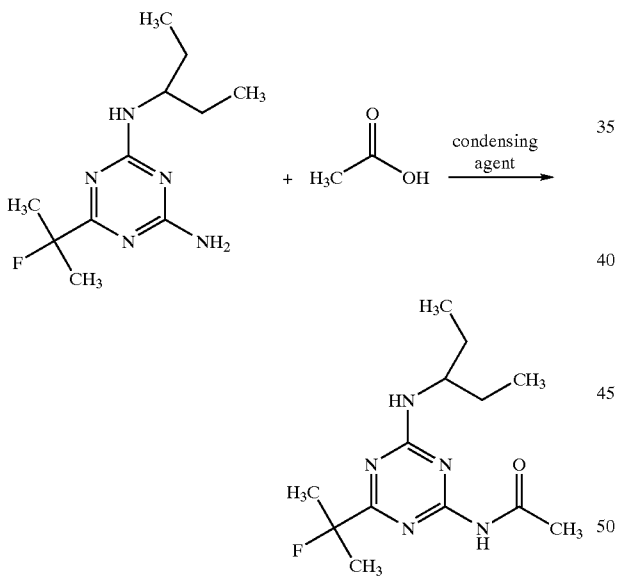

The formula (II) provides a general definition of the biguanides to be used as starting materials in the process according to the invention for preparing compounds of the general formula (I). In the general formula (II), A preferably or in particular has those meanings which have already been mentioned above in connection with the description of the compounds of the general formula (I) according to the invention as being preferred or as being particularly preferred for A.

Suitable acid adducts of compounds of the formula (II) are their addition products with protic acids, such as, for example, with hydrogen chloride, hydrogen bromide, sulphuric acid, methanesulphonic acid, benzenesulphonic acid and p-toluenesulphonic acid.

The starting materials of the general formula (II) have not yet been disclosed in the literature; as novel substances, they also form part of the subject-matter of the present application.

Among the intermediates of the general formula (II), particular mention may be made of the subgroup in which A represents $CHR^3R^4$, where $R^3$ represents optionally cyano-, halogen- or $C_1$–$C_4$-alkoxy-substituted $C_1$–$C_6$-alkyl and $R^4$ represents cyclohexyl which is optionally substituted by nitro, cyano, hydroxyl, halogen, by for its part in each case optionally cyano-, halogen- or $C_1$–$C_4$-alkoxy-substituted alkyl, alkoxy, alkylthio, alkylsulphinyl or alkylsulphonyl having in each case 1 to 6 carbon atoms or by for its part optionally cyano-, halogen- or $C_1$–$C_4$-alkyl-substituted cycloalkyl having 3 to 6 carbon atoms, and where $R^3$ preferably represents in each case optionally cyano-, fluorine-, chlorine-, methoxy-, ethoxy-, n- or i-propoxy-substituted methyl, ethyl, n- or i-propyl, n-, s-, i- or t-butyl, represents 2-fluoroethyl, 2-chloroethyl, 1-fluoroethyl, 3-fluoropropyl or 3-chloropropyl and $R^4$ preferably represents cyclohexyl which is optionally substituted by hydroxyl, fluorine, chlorine, by for its part in each case optionally fluorine-, chlorine-, methoxy-, ethoxy-, n- or i-propoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, or by for its part in each case optionally fluorine-, chlorine-, methyl-, ethyl-, n- or i-propyl-substituted cyclohexyl.

$R^6$ in all formulae of the compounds according to the invention preferably represents formyl or $C_1$–$C_3$-alkylcarbonyl and particularly preferably represents formyl, methylcarbonyl or ethylcarbonyl.

The novel biguanides of the general formula (II) are obtained when substituted amines of the general formula (VIII)

$$A-NH_2 \quad (VIII),$$

in which
A is as defined above,
and/or acid adducts of compounds of the general formula (VIII), such as, for example, the hydrochlorides
are reacted with cyanoguanidine ("dicyanodiamide") of the formula (IX)

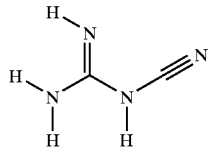

(IX)

if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf. the Preparation Examples).

After their preparation, the biguanides of the general formula (II) can also be employed directly, without intermediate isolation, for preparing the compounds of the general formula (I) by the process according to the invention.

Hydrochlorides according to the invention of the compounds of the general formula (II) which may be mentioned by way of example are: 1-methylbutylbiguanide hydrochloride, 1,2-dimethylpropylbiguanide hydrochloride, 1,3-dimethylbutylbiguanide hydrochloride, 1-ethylpropylbiguanide hydrochloride, 1-ethylbutylbiguanide hydrochloride, 1-ethyl-2-methylpropylbiguanide hydrochloride, 1-ethylpentylbiguanide hydrochloride, 1-ethyl-2-methylbutylbiguanide hydrochloride, 1-ethyl-3-methylbutylbiguanide hydrochloride, 1-ethyl-2,2-dimethylpropylbiguanide hydrochloride, 1-cyclopropylpropylbiguanide hydrochloride, 1-cyclopentylpropylbiguanide hydrochloride, 1-cyclohexylpropylbiguanide hydrochloride, 1-propylbutylbiguanide hydrochloride, 1-isopropylbutylbiguanide hydrochloride, 1-propylpentylbiguanide hydrochloride, 1-isopropyl-2-methylpropylbiguanide hydrochloride, 1-isopropylpentylbiguanide hydrochloride, 1-butylpentylbiguanide hydrochloride, 1-isobutylpentylbiguanide hydrochloride, 1,5-dimethylhexylbiguanide hydrochloride, 1-pentylhexylbiguanide hydrochloride, 1-ethyl-3-fluoropropylbiguanide hydrochloride, 3-chloro-1-ethylpropylbiguanide hydrochloride, 1-ethyl-2-fluoropropylbiguanide hydrochloride, 1-ethyl-4-fluorobutylbiguanide hydrochloride, 4-chloro-1-ethylbutylbiguanide hydrochloride, 2-trifluoromethylcyclohexylbiguanide hydrochloride, 3-trifluoromethylcyclohexyl-biguanide hydrochloride, 4-trifluoromethylcyclohexylbiguanide hydrochloride, 1,1-dimethyl-2-propynylbiguanide hydrochloride, 1-cyano-1-methylethylbiguanide hydrochloride etc.

The substituted amines of the general formula (VIII) required as precursors are known and/or can be prepared by processes known per se (cf. Bull. Soc. Chim. France 1952, 276–279; loc. cit. 1953, 974–981; Bull. Chem. Soc. Japan 57 (1984), 1570–1575; J. Am. Chem. Soc. 76 (1954), 4564–4570; loc. cit. 80 (1958), 5270–5272, JIKKEN KAGAKU KOUZA (Lectures of experimental chemistry), edited by the Chemical Society of Japan, Vol. 14, p. 1339 (1978) published by Maruzen; J. Am. Chem. Soc., 75, 3212 (1953); J. Am. Chem. Soc., 78, 860 (1956); J. Am. Chem. Soc., 66, 1517 (1944); Angew. Chem. Int. Ed., 7, 919 (1968); J. Chem. Soc., 2348 (1926); Synthesis, 717 (1980); Org. React., 3, 267 (1946); J. Chem. Soc., 267 (1941); Org. React., 3, 307 (1946); Org. React., 3, 337 (1946); J. Org. Chem. USSR, 16, 1031 (1980); Farmaco Ed. Sci., 22, 1037 (1967); J. Biol. Chem., 120, 772 (1937); WO 92/12121; EP-A 176327; CS-B233428; DE-A 2843480 etc.).

Hydrochlorides of the compounds of the general formula (VIII) according to the invention which may be mentioned by way of example are:

1-methylbutylamine hydrochloride, 1,2-dimethylpropylamine hydrochloride, 1,3-dimethylbutylamine hydrochloride, 1-ethylpropylamine hydrochloride, 1-ethylbutylamine hydrochloride, 1-ethyl-2-methylpropylamine hydrochloride, 1-ethylpentylamine hydrochloride, 1-ethyl-2-methylbutylamine hydrochloride, 1-ethyl-3-methylbutylamine hydrochloride, 1-ethyl-1,1-dimethylpropylamine hydrochloride, 1-cyclopropylpropylamine hydrochloride, 1-cyclopentylpropylamine hydrochloride, 1-cyclohexylpropylamine hydrochloride, 1-propylbutylamine hydrochloride, 1-isopropylbutylamine hydrochloride, 1-propylpentylamine hydrochloride, 1-isopropyl-2-methylpropylamine hydrochloride, 1-propylpentylamine hydrochloride, 1-isopropyl-2-methylpropylamine hydrochloride, 1-isopropylpentylamine hydrochloride, 1-butylpentylamine hydrochloride, 1-isobutylpentylamine hydrochloride, 1,5-dimethylhexylamine hydrochloride, 1-pentylhexylamine hydrochloride, 1-ethyl-3-fluoropropylamine hydrochloride, 3-chloro-1-ethylpropylamine hydrochloride, 1-ethyl-2-fluoropropylamine hydrochloride, 1-ethyl-4-fluorobutylamine hydro-chloride, 4-chloro-1-ethylbutylamine hydrochloride, 2-trifluoromethylcyclohexyl-amine hydrochloride, 3-trifluoromethylcyclohexylamine hydrochloride, 4-trifluoro-methylcyclohexylamine hydrochloride, 1,1-dimethyl-2-propinylamine hydrochloride, 1-cyano-1-methylethylamine hydrochloride etc.

The compound of the formula (IX) is a synthesis compound known in organic chemistry.

The formula (III) provides a general definition of the alkoxycarbonyl compounds further to be used as starting materials in the process according to the invention for preparing compounds of the general formula (I). In the general formula (III), $R^2$ preferably or in particular has that meaning which has already been mentioned above in connection with the description of the compounds of the general formula (I) according to the invention as being preferred or as being particularly preferred for $R^2$; $R^5$ preferably represents alkyl having 1 to 4 carbon atoms, in particular methyl or ethyl.

The starting materials of the general formula (III) are known chemicals for synthesis (see, for example, DE-A 4131242, EP-A 850911, EP-A 468681, JP-A 301844/1993, J. Org. Chem., 33, 4279 (1968) etc.). Examples of such compounds which may be mentioned are: methyl 1-fluoropropionate, ethyl 1-fluoropropionate, propyl 1-fluoropropionate, butyl 1-fluoropropionate, methyl 1-fluoro-1-methylpropionate, ethyl 1-fluoro-1-methylpropionate, propyl 1-fluoro-1-methylpropionate, butyl 1-fluoro-1-methylpropionate, etc.

The compounds of the general formula (Ia) which are used as starting compounds in the processes according to (b), (c), (d) and (e) are novel and can be prepared, for example, as a subgroup of compounds of the formula (I) by the process according to (a). Examples of such compounds which may be mentioned are: N-(1-methylbutyl)-6-(1-fluoro-1-methylethyl)-1,3,5-triazine-2,4-diamine, N-(1,2-dimethylpropyl-6-(1-fluoroethyl)-1,3,5-triazine-2,4-diamine, N-(1,3-dimethylbutyl)-6-(1-fluoro-1-methylethyl)-1,3,5-triazine-2,4-diamine, N-(1,5-dimethylhexyl)-6-(1-fluoro-1-methylethyl)-1,3,5-triazine-2,4-diamine, N-(1-ethylpropyl)-6-(1-fluoroethyl)-1,3,5-triazine-2,4-diamine, N-(1-ethylpropyl)-6-(1-fluoro-1-methylethyl)-1,3,5-triazine-2,4-diamine, N-(1-ethylbutyl)-6-(1-fluoroethyl)-1,3,5-triazine-2,4-diamine, N-(1-ethylbutyl)-6-(1-fluoro-1-methylethyl)-1,3,5-triazine-2,4-diamine, N-(1-ethyl-2-methylpropyl)-6-(1-fluoro-1-methylethyl)-1,3,5-triazine-2,4-diamine, N-(1-ethylpentyl)-6-(1-fluoro-1-methylethyl)-1,3,5-triazine-2,4-diamine etc.

The compounds of the formulae (IV), (V), (VI) and (VII) are known synthesis compounds of organic chemistry. In these compounds, $R^6$ preferably represents formyl, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl and particularly preferably represents formyl, methylcarbonyl, ethylcarbonyl, acetyl or propionyl. $R^6$ very particularly preferably represents formyl, ethylcarbonyl, methylcarbonyl. Compounds of the general formula (IV) which may be mentioned by way of example are: acetyl chloride, acetyl bromide, propionyl chloride.

Compounds of the general formula (V) which may be mentioned by way of example are: acetic anhydride and propionic anhydride.

Compounds of the general formula (VI) which may be mentioned by way of example are: methyl formate, ethyl formate, n-propyl formate, n-butyl formate, methyl acetate, ethyl acetate, n-propyl acetate, n-butyl acetate, methyl propionate, ethyl propionate, n-propyl propionate and n-butyl propionate.

Compounds of the general formula (VII) which may be mentioned by way of example are: formic acid, acetic acid and propionic acid.

The process according to the invention according to (a) for preparing the compounds of the general formula (I) is preferably carried out using a diluent. Suitable diluents for carrying out the process according to the invention are, in addition to water, especially inert organic solvents. These include, in particular, aliphatic, alicyclic or aromatic, optionally halogenated, hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dibutyl ether, dioxane, dimethoxymethane (DME), tetrahydrofuran or ethylene glycol dimethyl ether or ethylene glycol diethyl ether; ketones, such as acetone, methyl ethyl ketone (MEK), butanone, methyl isopropyl ketone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethylsulphoxide; alcohols, such as methanol, ethanol, n- or i-propanol, butanol, ethylene glycol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyldicyclohexylamine, N,N-dimethyl-aniline, N,N-diethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 1,1,4,4-tetramethylmethylenediamine (TMEDA), 4-dimethylamino-pyridine, N-methyl-piperidine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU), and also organolithium compounds, such as, for example, methyllithium, n-butyllithium, sec-butyllithium, tert-butyllithium, phenyllithium, lithium diisopropylamide, n-butyllithium DABCO, n-butyllithium. DBU, n-butyllithium TMEDA etc.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts, 1 mol of a compound of the general formula (II) can be reacted, for example, with 1–2 mol of a compound of the general formula (III) in the presence of a base, for example 1–2 mol of sodium ethoxide, in the diluent ethanol. However, it is also possible to employ a relatively large excess of one of the components. The reaction is generally carried out in a suitable diluent in the presence of a reaction auxiliary, and the reaction mixture is generally stirred at the required temperature for a plurality of hours. Work-up is carried out by customary methods (cf. the Preparation Examples).

The process according to the invention according to (b), (c), (d) or (e) for preparing the compounds of the general formula (I) is preferably carried out using a diluent. Suitable diluents for carrying out the process according to the invention are, in addition to water, especially inert organic solvents. These include, in particular, aliphatic, alicyclic or aromatic, optionally halogenated, hydrocarbons, such as, for example, benzene, toluene, xylene, chlorobenzene, dichlorobenzene, dichloromethane, chloroform, 1,2-dichloroethane, carbon tetrachloride; ethers, such as diethyl ether, methyl ethyl ether, diisopropyl ether, dibutyl ether, dioxane, dimethoxymethane (DME), tetrahydrofuran or ethylene glycol dimethyl ether or ethylene glycol diethyl ether; ketones, such as acetone, methyl ethyl ketone (MEK), butanone, methyl isopropyl ketone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl-sulphoxide; alcohols, such as methanol, ethanol, n- or i-propanol, butanol, ethylene glycol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes according to the invention according to (b), (c) or (d) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethylcyclohexylamine, dicyclohexylamine, ethyldicyclohexylamine, N,N-dimethyl-aniline, N,N-diethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 1,1,4,4-tetramethylmethylenediamine (TMEDA), 4-dimethylamino-pyridine, N-methyl-piperidine, 1,4-diazabicyclo[2.2.2]octane (DABCO), 1,5-diazabicyclo[4.3.0]-non-5-ene (DBN) or 1,8-diazabicyclo[5.4.0]-undec-7-ene (DBU).

The process according to the invention according to (e) is preferably carried out in the presence of a condensing agent. Examples of such condensing agents which may be mentioned are: dicyclohexylcarbodiimide, acetic anhydride, thionyl chloride, phosphorus pentachloride, phosphorus oxychloride, aluminium oxide, silicon tetrachloride, titanium tetrachloride etc.

When carrying out the processes according to the invention according to (b), (c), (d) or (e), the reaction temperatures can be varied within a relatively wide range. In general, the processes are carried out at temperatures between 0° C. and 150° C., preferably between 0° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention according to (b), the starting materials are generally employed in approximately equimolar amounts, 1 mol of a compound of the general formula (Ia) can be reacted, for example, with 0.8–2.0 mol of a compound of the general formula (IV) in the presence of a base, for example 1–3 mol of triethylamine. However, it is also possible to employ a relatively large excess of one of the components.

For carrying out the process according to the invention according to (c), the starting materials are generally employed in approximately equimolar amounts, 1 mol of a compound of the general formula (Ia) can be reacted, for example, with 0.8–2.0 mol of a compound of the general formula (V) in the presence of a base, for example 1–3 mol of triethylamine. However, it is also possible to employ a relatively large excess of one of the components.

For carrying out the process according to the invention according to (d), the starting materials are generally employed in approximately equimolar amounts, 1 mol of a compound of the general formula (Ia) can be reacted, for example, with 0.8–2.0 mol of a compound of the general formula (VI) in the presence of a base, for example 1–3 mol of sodium methoxide. However, it is also possible to employ a relatively large excess of one of the components.

For carrying out the process according to the invention according to (e), the starting materials are generally employed in approximately equimolar amounts, 1 mol of a compound of the general formula (Ia) can be reacted, for example, with 0.8–2.0 mol of a compound of the general formula (IV) in the presence of a condensing agent, for example dicyclohexylcarbodiimide. However, it is also possible to employ a relatively large excess of one of the components.

The active compounds according to the invention are particuliarly suitable for use as defoliants, desiccants, haulmkillers and, especially, as weedkillers. Weeds, in the broadest sense, are to be understood as all plants which grow in locations where they are undesired. Whether the substances according to the invention act as total or selective herbicides depends essentially on the amount used. The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Aegilop, Phalaris.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

In a use form that is emphasized here, the active compounds according to the invention can also be used in connection with transgenic plants. In this case, a synergistic effect was observed.

The active compounds according to the invention are suitable, depending on the concentration, for the total control of weeds, for example on industrial terrain and rail tracks, and on paths and squares with or without tree plantings. Equally, the active compounds according to the invention can be employed for controlling weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pastures, and for the selective control of weeds in annual crops.

The compounds of the formula (I) according to the invention have strong herbicidal activity and a broad activity spectrum when used on the soil and on above-ground parts of the plants. To a certain extent, they are also suitable for the selective control of monocotyledonous and dicotyledonous weeds, in particular in monocotyledonous crops, both pre- and post-emergence.

The active compounds can be converted into the customary formulations, such as solutions, emulsions, wettable powders, suspensions, powders, dusts, pastes, soluble powders, granules, suspension emulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surface-active agents, that is emulsifiers and/or dispersants and/or foam-formers.

In the case of the use of water as an extender, organic solvents can, for example, also be used as auxiliary solvents. Suitable liquid solvents are mainly: aromatics, such as xylene, toluene or alkylnaphthalenes, chlorinated aromatics or chlorinated aliphatic hydrocarbons, such as chlorobenzene, chloroethylenes or methylene chloride, aliphatic hydrocarbons, such as cyclohexane or paraffins, for example mineral oil fractions, mineral or vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally contain between 0.1 and 95 percent by weight of active compound, preferably between 0.5 and 90%.

For controlling weeds, the active compounds according to the invention, as such or in the form of their formulations, can also be used as mixtures with known herbicides, ready mixes or tank mixes being possible.

Examples of known herbicides which are suitable for the mixtures are acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazone, chlorimuron(-ethyl), chlornitrofen, chlorosulfuron, chlortoluron, cinidone(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamide, dimexyflam, dinitramine, diphenamide, diquat, dithiopyr, diuron, dymron, epropodan, EPTC, esprocarb, ethalfluralin, ethametsulfuron(-methyl), ethofumesate, ethoxyfen, ethoxysulfuron, etobenzanid, fenoxaprop(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate (-ammonium), glyphosate(-isopropylammonium), halosafen, haloxyfop (-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop (-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, thiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellants, plant nutrients and soil conditioners is also possible.

To improve compatibility with crop plants, it is also possible to mix the compounds of the general formula (I) with one or more safeners, and the safener 1-(α,α-dimethylbenzyl)-3-p-tolylurea may be mentioned as an example here.

The active compounds may be applied as such, in the form of their formulations or of the use forms prepared therefrom by further dilution, such as ready-to-use solutions, suspensions, emulsions, powders, pastes and granules. They are applied in the customary manner, for example by pouring, spraying, atomizing, broadcasting.

The active compounds according to the invention can be applied either before or after plant emergence. They may also be incorporated into the soil prior to planting.

The amount of active compound applied can vary within a substantial range. It depends essentially on the nature of the desired effect. In general, the application rates are between 1 g and 10 kg of active compound per hectare of soil surface, preferably between 5 g and 5 kg per ha.

Preparation and use of the active compounds according to the invention can be seen from the examples which follow.

PREPARATION EXAMPLES

Example 1

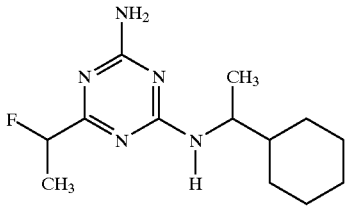

At room temperature (approximately 20° C.), a solution of 4.7 g (85 mmol) of sodium methoxide in 100 ml of methanol is added with stirring to a mixture of 20 g (80 mmol) of (R,S)-1-cyclohexyl-ethyl-biguanide hydrochloride, 10 g (80 mmol) of methyl 2-fluoropropanoate and 100 ml of methanol, and the reaction mixture is stirred at room temperature for 15 hours. After concentration under waterpump vacuum, the residue is shaken with methylene chloride and water and the organic phase is dried with sodium sulphate and filtered. The solvent is carefully distilled off under reduced pressure from the filtrate.

This gives 9.2 g (43% of theory) of (R,S)-N'-(1-cyclohexyl-ethyl)-6-(1-fluoro-ethyl)-1,3,5-triazine-2,4-diamine as an amorphous residue.

logP=1.83[a)]

Example 2

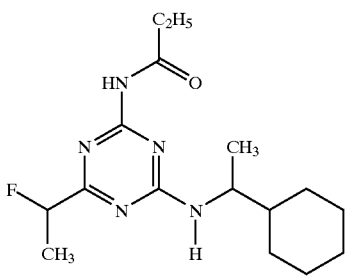

A mixture of 3.5 g (13 mmol) of (R,S)-N'-(1-cyclohexyl-ethyl)-6-(1-fluoroethyl)-1,3,5-triazine-2,4-diamine (cf. Example 1) and 25 ml of propionic anhydride is stirred at 130° C. for 60 minutes. The volatile components are then carefully distilled off under reduced pressure.

This gives 3.8 g (90% of theory) of (R,S)-N-[4-(1-cyclohexyl-ethylamino)-6-(1-fluoro-ethyl)-1,3,5-triazin-2-yl]-propionamide as an amorphous residue.

logP=3.14[a)]

Example 3

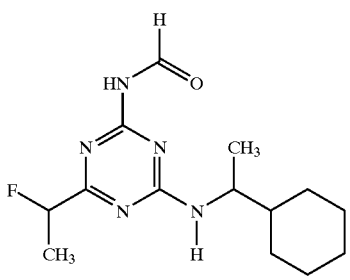

A mixture of 3.5 g (13 mmol) of (R,S)-N'-(1-cyclohexyl-ethyl)-6-(1-fluoro-ethyl)-1,3,5-triazine-2,4-diamine (cf. Example 1), 2.5 g (21 mmol) of N,N-dimethylformamide dimethyl acetal and 50 ml of 1,4-dioxane is stirred at room temperature (approximately 20° C.) for 15 hours. After addition of 80 ml of water and 3 ml of conc. hydrochloric acid, the mixture is stirred at room temperature for another 60 minutes. The crystalline product is subsequently isolated by filtration with suction.

This gives 1.8 g (47% of theory) of (R,S)-N-[4-(1-cyclohexyl-ethylamino)-6-(1-fluoro-ethyl)-1,3,5-triazin-2-yl]-formamide of melting point 127° C.

logP=3.04[a)]

Example 4

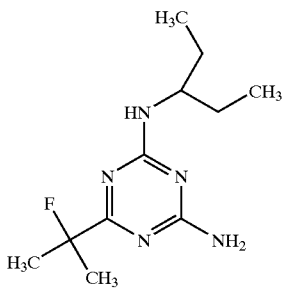

94 g of ethylpropylamine hydrochloride are suspended in 50 ml of 1,2-dichlorobenzene. 3.36 g of cyanoguanidine are added, and the mixture is then stirred at from 150° C. to 170° C. for 3 hours. The crystalline product is subsequently isolated by filtration with suction and washed three times with ether (10 ml). The volatile solvent fractions are then carefully distilled off under reduced pressure, giving the ethylpropylbiguanide which is reacted further without any further purification steps.

Subsequently, 1.10 g of metallic sodium are admixed with 150 ml of methanol. After the sodium has reacted completely, 5.29 g of ethylpropylbiguanide are added to the mixture, and the mixture is stirred at room temperature for 48 hours. The volatile methanol is then distilled off under reduced pressure. The solid residue is admixed with 80 ml of water and the mixture is extracted with ethyl acetate (120 ml). The organic phase is dried over anhydrous sodium sulphate and the solvent is distilled off under reduced pressure. Purification by column chromatography on a silica gel phase (mobile phase: ether/n-hexane=1:1) gives the desired product.

3.20 g (33% of theory) of N-(1-ethylpropyl)-6-(1-fluoro-1-methylethyl)-1,3,5-triazine-2,4-diamine of melting point 104–106° C. are obtained.

Example 5

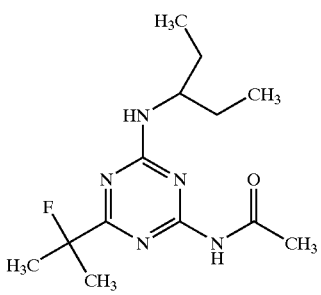

1 g of N-(1-ethylpropyl)-6-(1-fluoro-1-methylethyl)-1,3,5-triazine-2,4-diamine and 5.63 g of triethylamine are suspended in 30 ml of tetrahydrofuran. At a temperature of 5° C., 3.39 g of acetyl chloride are added and the mixture is heated under reflux for 2 hours. The reaction mixture is admixed with 60 ml of a saturated sodium bicarbonate solution and extracted with 80 ml of ethyl acetate. The organic phase is dried over anhydrous magnesium sulphate, giving a crude product which, after purification by column chromatography on a silica gel phase (mobile phase: ether/n-hexane=1:1) affords the desired product.

In almost quantitative yield, 1.17 g of N-acetyl-N'-(1-ethylpropyl)-6-(1-fluoro-1-methylethyl)-1,3,5-triazine-2,4-diamine of melting point 109–111° C. are obtained.

Analogously to Examples 1 to 5, and in accordance with the general description of the preparation process according to the invention, it is also possible to prepare, for example, the compounds of the general formula (I) listed in Table 1 below.

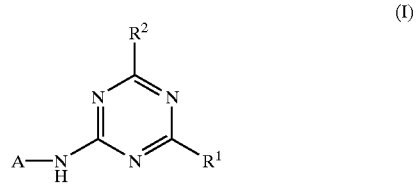

(I)

TABLE 1

Examples of compounds of the formula (I)

| Ex. No. | A | $R^1$ | $R^2$ | Physical data and stereochem. details (mp = melting point) |
|---|---|---|---|---|
| 6 | CH₃-CH(cyclohexyl)- | $NH_2$ | $CF_2Cl$ | logP = 3.51[a] (racemate) |
| 7 | CH₃-CH(cyclohexyl)- | $NH_2$ | $CF(CH_3)_2$ | logP = 1.93[a] (racemate) |
| 8 | CH₃-CH(cyclohexyl)- | $C_2H_5$, H-N(CH₃)-C(=O)- | $CF_2Cl$ | logP = 4.23[a] (racemate) |
| 9 | CH₃-CH(cyclohexyl)- | $C_2H_5$, H-N(CH₃)-C(=O)- | $CF(CH_3)_2$ | logP = 3.30[a] (racemate) |
| 10 | CH₃-CH(cyclohexyl)- | H, H-N(CH₃)-C(=O)- | $CHFCH_3$ | logP = 3.04[a] (racemate) |

TABLE 1-continued

Examples of compounds of the formula (I)

| Ex. No. | A | R¹ | R² | Physical data and stereochem. details (mp = melting point) |
|---|---|---|---|---|
| 11 | 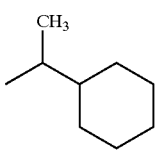 | 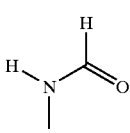 | CF(CH$_3$)$_2$ | logP = 3.44[a) (racemate) |
| 12 | 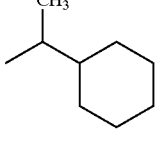 | NH$_2$ | CHFCH$_3$ | logP = 1.83[a) (R enantiomer) |
| 13 | 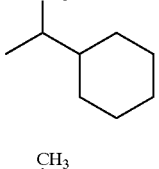 | NH$_2$ | CF(CH$_3$)$_2$ | logP = 1.93[a) (R enantiomer) |
| 14 | 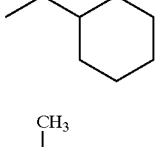 | NH$_2$ | CHCl$_2$ | logP = 3.21[a) (R enantiomer) |
| 15 | 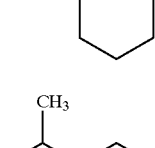 | 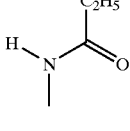 | CHFCH$_3$ | logP = 3.11[a) (R enantiomer) |
| 16 | 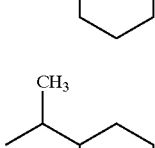 | 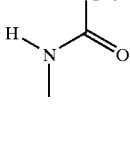 | CF(CH$_3$)$_2$ | logP = 3.25[a) (R enantiomer) |
| 17 | 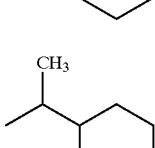 | 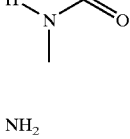 | CHCl$_2$ | logP = 2.93[a) (R enantiomer) |
| 18 | 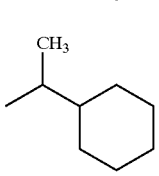 | NH$_2$ | CHFCH$_3$ | logP = 1.82[a) (S enantiomer) |
| 19 |  | NH$_2$ | CF(CH$_3$)$_2$ | logP = 1.92[a) (S enantiomer) |

TABLE 1-continued

Examples of compounds of the formula (I)

| Ex. No. | A | R¹ | R² | Physical data and stereochem. details (mp = melting point) |
|---|---|---|---|---|
| 20 | 1-cyclohexylethyl (CH₃) | NH₂ | CHCl₂ | logP = 3.20[a] (S enantiomer) |
| 21 | 1-cyclohexylethyl (CH₃) | N(CH₃)C(O)C₂H₅ | CHFCH₃ | logP = 3.11[a] (S enantiomer) |
| 22 | 1-cyclohexylethyl (CH₃) | N(CH₃)C(O)C₂H₅ | CF(CH₃)₂ | logP = 3.26[a] (S enantiomer) |
| 23 | 1-cyclohexylethyl (CH₃) | N(CH₃)C(O)C₂H₅ | CHCl₂ | logP = 2.93[a] (S enantiomer) |
| 24 | 1-cyclohexylpropyl (C₂H₅) | NH₂ | CHFCH₃ | logP = 2.05[a] (R enantiomer) |
| 25 | 1-cyclohexylpropyl (C₂H₅) | NH₂ | CF(CH₃)₂ | logP = 2.13[a] (R enantiomer) |
| 26 | 1-cyclohexylpropyl (C₂H₅) | NH₂ | CHFCH₃ | logP = 2.05[a] (s enantiomer) |
| 27 | 1-cyclohexylpropyl (C₂H₅) | NH₂ | CF(CH₃)₂ | logP = 2.12[a] (S enantiomer) |
| 28 | CH₃CH₂CH₂CH(CH₃) | NH₂ | (CH₃)₂CF | mp 108–111° C. (racemate) |
| 29 | (CH₃)₂CHCH₂CH(CH₃) | NH₂ | (CH₃)₂CF | $n^{20}_D$ 1.51590 (racemate) |
| 30 | (CH₃)₂CHCH₂CH(CH₃) | NH₂ | (CH₃)₂CF | mp 123–125° C. (racemate) |
| 31 | (CH₃)₂CHCH₂CH₂CH₂CH(CH₃) | NH₂ | (CH₃)₂CF | mp 107–110° C. (racemate) |
| 32 | (C₂H₅)CH(C₂H₅) | NH₂ | CH₃CHF | mp 89–90° C. |

TABLE 1-continued

Examples of compounds of the formula (I)

| Ex. No. | A | R¹ | R² | Physical data and stereochem. details (mp = melting point) |
|---|---|---|---|---|
| 33 | (C₂H₅)CH(C₂H₅) | NH₂ | (CH₃)₂CF | (racemate) mp 104–106° C. |
| 34 | (C₂H₅)CH(C₂H₅) | NHCOCH₃ | (CH₃)₂CF | (racemate) mp 109–111° C. |
| 35 | F₃C— (cyclohexyl with methyl) | NH₂ | (CH₃)₂CF | (racemate) $n^{20}_D$ 1.4780 (racemate) |

The logP values given in Table 1 were determined in accordance with EEC Directive 79/831 Annex V.A8 by HPLC (High Performance Liquid Chromatography) using a reversed-phase column (C 18). Temperature: 43° C.

(a) Mobile phase for the determination in the acidic range: 0.1% aqueous phosphoric acid, acetonitrile; linear gradient from 10% acetonitrile to 90% acetonitrile—the corresponding data in Table 1 are labelled[a].

(b) Mobile phase for the determination in the neutral range: 0.01 molar aqueous phosphate buffer solution, acetonitrile; linear gradient from 10% acetonitrile to 90% acetonitrile—the corresponding data in Table 1 are labelled[b].

Calibration was carried out using unbranched alkan-2-ones (having from 3 to 16 carbon atoms) with known logP values (the logP values were determined using the retention times, by linear interpolation between two successive alkanones).

The lambda max values were determined using the UV spectra from 200 nm to 400 nm in the maxima of the chromatographic signals.

Starting Materials of the Formula (II)

Example (II-1)

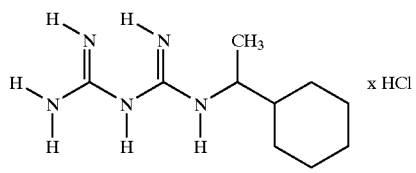 x HCl

A mixture of 28.4 g (0.4 mol) of (R,S)-1-cyclohexyl-ethylamine, 350 ml of toluene, 150 ml of decane and 48 g of 30% strength aqueous hydrochloric acid is subjected to an azeotropic distillation. Liquid is distilled off until an internal temperature of 135° C. is reached. At this temperature, 33.6 g (0.4 mol) of cyanoguanidine are added to the remaining mixture, and the reaction mixture is stirred at 135° C. for two hours. The mixture is subsequently allowed to cool to room temperature, about 100 ml of acetone are added and the crystalline product is isolated by filtration with suction.

This gives 67.9 g (69% of theory) of (R,S)-1-cyclohexyl-ethyl-biguanide hydrochloride as a solid product.

Analogously to Example II-1, it is also possible to prepare, for example, the compounds of the general formula (II) listed in Table 2 below.

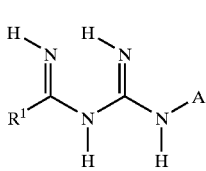

(II)

TABLE 2

Examples of compounds of the formula (II)
These compounds are in each case the hydrochlorides

| Ex. No. | A | R¹ | Physical data and stereochem. details |
|---|---|---|---|
| II-2 | CH₃ (isopropyl-cyclohexyl) | NH₂ | (R enantiomer) |
| II-3 | CH₃ (isopropyl-cyclohexyl) | NH₂ | (S enantiomer) |
| II-4 | C₂H₅ (sec-butyl-cyclohexyl) | NH₂ | (R enantiomer) |
| II-5 | C₂H₅ (sec-butyl-cyclohexyl) | NH₂ | (S enantiomer) |

USE EXAMPLES

Example A-1

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 litres of water per hectare.

After three weeks, the degree of damage to the plants is rated in % damage in comparison to the development of the untreated control.

The figures denote:

0%=no effect (like untreated control)
100%=total destruction

In this test, for example, the compound of Preparation Example 1 exhibits strong action against weeds, whilst being tolerated very well by crop plants, such as, for example, maize.

Example A-2

| Pre-emergence test | |
|---|---|
| Solvent: | 5 parts by weight of acetone |
| Emulsifier: | 1 part by weight of benzyloxy polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants (*Echinocloa crus galli, Setaria viridis, Amaranthus lividus* and *Polygonum blumei* MEISSN) are sown in normal soil. The soil is sprayed with the preparation of active compound such that the particular amount of active compound desired is applied per unit area.

After four weeks, the degree of damage to the plants is rated in % damage in comparison to the development of the untreated controls.

The figures denote:

0%=no effect (like untreated control)
100%=total destruction

In this test, for example, the compounds of Preparation Examples 32, 33, 34 and 35 exhibit strong action against the abovementioned weeds.

Example B-1

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 1, 2, 3, 4, 5, 6, 7, 8 and 9 exhibit strong action against weeds, and some of them are tolerated well by crop plants, such as, for example, maize.

Example B-2

| Post-emergence test | |
|---|---|
| Solvent: | 5 parts by weight of acetone |
| Emulsifier: | 1 part by weight of benzyloxy polyglycol ether |

To produce a suitable preparation of active compound, 1 part by weight of active compound is mixed with the stated amount of solvent, the stated amount of emulsifier is added and the concentrate is diluted with water to the desired concentration.

Test plants (*Echinocloa crus galli, Setaria viridis, Amaranthus lividus* and *Polygonum blumei* MEISSN) which, on average, are in the 2-leaf stage, are sprayed with the preparation of active compound such that the particular amounts of active compound desired are applied per unit area.

After three weeks, the degree of damage to the plants is rated in % damage in comparison to the development of the untreated control.

The figures denote:

0%=no effect (like untreated control)
100%=total destruction

In this test, for example, the compounds of Preparation Examples 28, 29, 31 and 35 exhibit strong action against the abovementioned weeds.

TABLE A-1

Pre-emergence test/greenhouse

| Active compound of Preparation Example No. | Application rate g of ai./ha | Maize | Abutilon | Amaranthus |
|---|---|---|---|---|
| 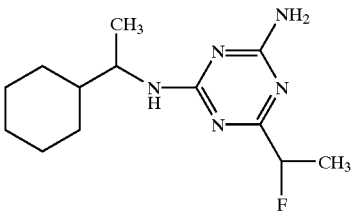 (1) | 500 | 0 | 80 | 100 |

TABLE B-1-1

Post-emergence test/greenhouse

| Active compound of Preparation Example No. | Application rate g of ai./ha | Maize | Setaria | Amaranthus | Sinapis |
|---|---|---|---|---|---|
| 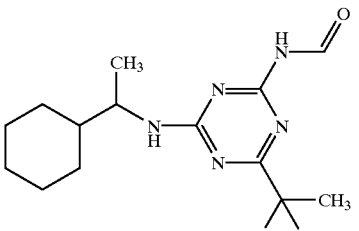 (9) | 500 | 30 | 90 | 95 | 100 |

TABLE B-1-2

Post-emergence test/greenhouse

| Active compound of Preparation Example No. | Application rate g of ai./ha | Setaria | Abutilon | Amaranthus | Sinapis |
|---|---|---|---|---|---|
| 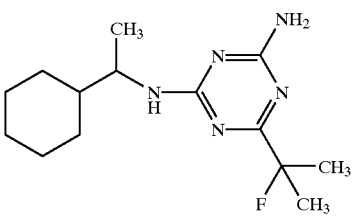 (5) | 500 | 95 | 90 | 100 | 95 |
| 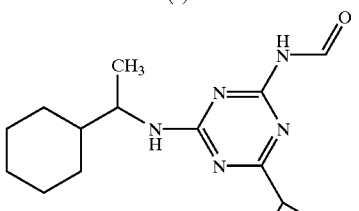 (3) | 500 | 100 | 90 | 100 | 100 |

TABLE B-1-3
Post-emergence test/greenhouse
| Active compound of Preparation Example No. | Application rate g of ai./ha | Setaria | Amaranthus | Sinapis | Xanthium |
|---|---|---|---|---|---|
| 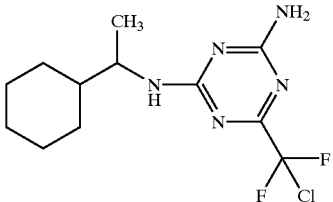 (4) | 500 | 100 | 100 | 100 | 100 |
| 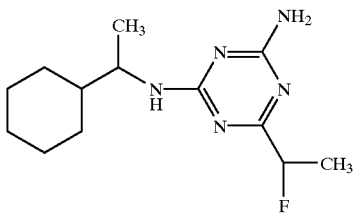 (1) | 500 | 100 | 100 | 100 | 100 |
TABLE B-1-4
Post-emergence test/greenhouse
| Active compound of Preparation Example No. | Application rate g of ai./ha | Setaria | Amaranthus | Sinapis | Xanthium |
|---|---|---|---|---|---|
| 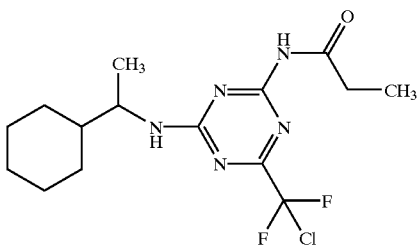 (6) | 500 | 100 | 100 | 100 | 100 |
| 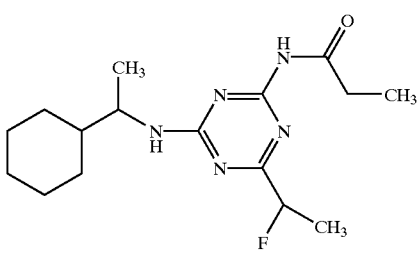 (2) | 500 | 100 | 100 | 100 | 100 |

TABLE B-1-5

Post-emergence test/greenhouse

| Active compound of Preparation Example No. | Application rate g of ai./ha | Setaria | Amaranthus | Sinapis | Xanthium |
|---|---|---|---|---|---|
| 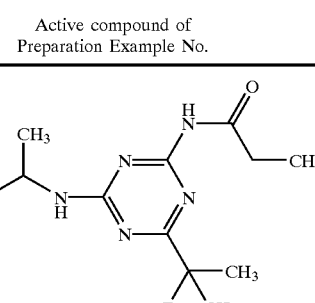 (7) | 500 | 100 | 100 | 100 | 100 |
| 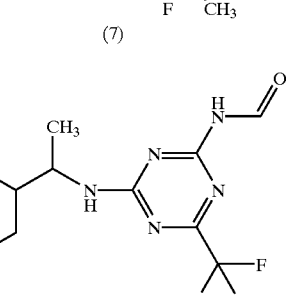 (8) | 500 | 100 | 100 | 100 | 100 |

FORMULATION EXAMPLES

Formulation Example 1
(Granules)

25 parts by weight of water are added to a mixture of 10 parts by weight of the compound from Preparation Example 28, 30 parts by weight of bentonite (montmorillonite), 58 parts by weight of talc and 2 parts by weight of ligninsulphonate salt. The components are kneaded well with one another and used to prepare, in an extrusion granulator, granules (particle size 10–40 mesh) which are dried at 40–50° C.

Formulation Example 2
(Emulsifiable Concentrate)

30 parts by weight of the compound from Preparation Example 32, 55 parts by weight of xylene, 8 parts by weight of polyoxyethylene alkylphenyl ether and 7 parts by weight of calcium alkylbenzenesulphonate are mixed and, with stirring, processed to give an emulsifiable concentrate.

Formulation Example 3
(Wettable Powder)

15 parts by weight of the compound from Preparation Example 33, 80 parts by weight of a mixture (1:5) of "white carbon" (fine particles of hydrated amorphous silica) and pulverized loam and 3 parts by weight of a sodium naphthalenesulphonate/formaline condensate are comminuted and mixed to give a wettable powder.

Formulation Example 4
(Wettable Granules)

20 parts by weight of the compound from Preparation Example 35, 30 parts by weight of sodium ligninsulphonate, 15 parts by weight of bentonite and 35 parts by weight of calcined pulverulent diatomaceous earth are intensively mixed with water.

The resulting product is granulated by extrusion through a 0.3 mm sieve. Drying gives wettable granules.

What is claimed is:

1. A compound of the formula (I)

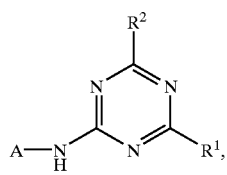

wherein

A represents $CHR^3R^4$ or represents $C_3$–$C_6$-alkynyl or $C_1$–$C_4$-cyanoalkyl, wherein
$R^3$ and $R^4$ independently represent unsubstituted or cyano-, halogen- or $C_1$–$C_4$-alkoxy-substituted $C_1$–$C_6$-alkyl, represent $C_1$–$C_4$-halogenoalkyl or represent $C_3$–$C_7$-cycloalkyl which is unsubstituted or substituted by nitro, cyano, hydroxyl, halogen, by unsubstituted or cyano- halogen- or $C_1$–$C_4$-alkoxy-substituted alkyl, alkoxy, alkoxy, alkylthio, alkylsulphinyl or alkylsulphonyl having 1 to 6 carbon atoms or by unsubstituted or cyano-, halogen- or $C_1$–$C_4$-alkyl-substituted cycloalkyl having 3 to 6 carbon atoms with the proviso that the total number of carbon atoms of $R^3$ and $R^4$ together is greater than 3, $R^1$ represents amino, formylamino, ethylcarbonylamino, or methylcarbonylamino, and $R^2$ represents 1-fluoroethyl, difluorochloromethyl, dichloromethyl or 1-fluoro-1-methylethyl.

2. The compound of claim 1, wherein

A represents $CHR^3R^4$ or 1,1-dimethyl-2-propynyl or 1-cyano-methylethyl, wherein $R^3$ and $R^4$ independently represent methyl, ethyl, n- or i-propyl, or represent 2-fluoroethyl, 2-chloroethyl, 1-fluoroethyl, 3-fluoropropyl or 3-chloropropyl or represent cyclopentyl or cyclohexyl with the proviso that the total number of carbon atoms of $R^3$ and $R^4$ together is greater than 3, $R^1$ represents amino, formylamino, ethylcarbonylamino or methylcarbonylamino, and $R^2$ represents 1-fluoroethyl, difluorochloromethyl, dichloromethyl or 1-fluoro-1-methylethyl.

3. A process for preparing the compound of claim 1, comprising reacting a biguanide of the formula (II)

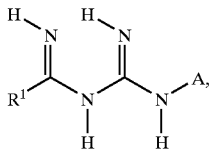

(II)

wherein

A and $R^1$ are as defined in claim 1, and/or acid adducts of compounds of the formula (II), with an alkoxycarbonyl compound of the formula (III)

$$R^2\text{---}CO\text{---}OR^5 \qquad (III),$$

wherein $R^2$ is as defined in claim 1 and $R^5$ represents alkyl, or reacting a 1,3,5-triazine of the formula (Ia)

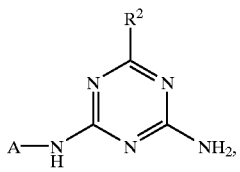

(Ia)

where A and R are as defined in claim 1, with a carbonyl halide of the formula (IV)

$$R^6X^2 \qquad (IV),$$

wherein $R^6$ represents formyl or represents unsubstituted or cyano-, halogen- or $C_1$–$C_4$-alkoxy-substituted alkylcarbonyl having 1 to 6 carbon atoms in the alkyl group and $X^2$ represents chlorine or bromine, in the presence of a diluent, or reacting a compound of the formula (Ia) in which $R^1$ represents amino with a carboxylic anhydride of the formula (V)

$$R^6OR^6 \qquad (V),$$

where $R^6$ is as defined above, in the presence of a diluent, or reacting a compound of the formula (Ia) in which $R^1$ represents amino with a carboxylic ester of the formula (VI)

$$R^6OR^5 \qquad (VI),$$

where $R^5$ and $R^6$ are as defined above, in the presence of a diluent, or reacting a compound of the formula (Ia) in which $R^1$ represents amino with a carboxylic acid of the formula (VII)

$$R^6OH \qquad (VII),$$

where $R^6$ is as defined above, in the presence of a diluent.

4. A compound of the formula (II)

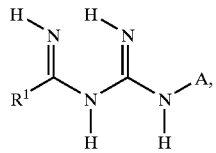

(II)

wherein

A represents $CHR^3R^4$ wherein
$R^3$ represents $C_1$–$C_6$-alkyl, and
$R^4$ represents $C_3$–$C_7$-cycloalkyl, and $R^1$ represents amino, formylamino, ethylcarbonylamino, or methylcarbonylamino, or an acid adduct of a compound of the formula (II).

5. The compound of claim 4, wherein

A represents $CHR^3R^4$,
wherein $R^3$ represents methyl or ethyl and $R^4$ represents cyclohexyl.

6. A method for controlling plant growth, comprising applying an effective amount of one or more compounds of claim 1 to a plant and/or its habitat.

7. A herbicidal composition, comprising at least one compound of claim 1 and one or more of extenders and surfactants.

* * * * *